US011850143B2

(12) United States Patent
Huang et al.

(10) Patent No.: US 11,850,143 B2
(45) Date of Patent: Dec. 26, 2023

(54) TISSUE REPAIR DEVICE AND METHOD FOR USING THE SAME

(71) Applicant: INDUSTRIAL TECHNOLOGY RESEARCH INSTITUTE, Hsinchu (TW)

(72) Inventors: Chih-Chieh Huang, Zhunan Township (TW); Jeng-Liang Kuo, Hsinchu (TW); Hui-Ting Huang, Zhubei (TW); Shiun-Yin Chang, Changhua (TW); Meng-Hsueh Lin, Taoyuan (TW); Cheng-Yi Wu, Zhubei (TW); Lih-Tao Hsu, Taoyuan (TW); Pei-I Tsai, Hsinchu (TW); Hsin-Hsin Shen, Zhudong Township (TW); Chih-Yu Chen, Zhubei (TW); Kuo-Yi Yang, Hsinchu (TW); Chun-Hsien Ma, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 17/243,858

(22) Filed: Apr. 29, 2021

(65) Prior Publication Data

US 2021/0338414 A1 Nov. 4, 2021

(30) Foreign Application Priority Data

Apr. 30, 2020 (TW) .................................. 109114515
Apr. 28, 2021 (TW) .................................. 110115426

(51) Int. Cl.
*A61F 2/08* (2006.01)

(52) U.S. Cl.
CPC ..... *A61F 2/0811* (2013.01); *A61F 2210/0076* (2013.01); *A61F 2220/0075* (2013.01);
(Continued)

(58) Field of Classification Search
CPC ..................................................... A61F 2/0811
See application file for complete search history.

(56) References Cited

U.S. PATENT DOCUMENTS

| | | | | | |
|---|---|---|---|---|---|
| 4,735,843 | A | * | 4/1988 | Noda | A61L 15/42 525/902 |
| 5,023,124 | A | * | 6/1991 | Kobayashi | A61F 13/51305 428/913 |

(Continued)

FOREIGN PATENT DOCUMENTS

| | | |
|---|---|---|
| CN | 102470189 A | 5/2012 |
| CN | 104399117 A | 3/2015 |

(Continued)

OTHER PUBLICATIONS

Taiwanese Office Action and Search Report for Taiwanese Application No. 110115426, dated Dec. 6, 2021.

*Primary Examiner* — Jacqueline Woznicki
(74) *Attorney, Agent, or Firm* — Birch, Stewart, Kolasch & Birch, LLP

(57) ABSTRACT

A tissue repair device and a method for using the same are provided. The tissue repair device includes a body portion and at least one wire. The body portion includes an inner layer and an outer layer. The inner layer is close to a tissue, wherein the inner layer includes a hydrophilic structure, and the outer layer includes a hydrophobic structure. The wire is connected to the body portion to fix the body portion to the tissue.

11 Claims, 16 Drawing Sheets

(52) U.S. Cl.
CPC ............... *A61F 2230/0069* (2013.01); *A61F 2230/0091* (2013.01); *A61F 2250/0017* (2013.01); *A61F 2250/0056* (2013.01)

(56) References Cited

U.S. PATENT DOCUMENTS

| | | | | |
|---|---|---|---|---|
| 5,061,283 | A * | 10/1991 | Silvestrini | A61B 17/1146 128/898 |
| 5,891,076 | A * | 4/1999 | Fabo | A61L 15/26 602/58 |
| 5,939,339 | A * | 8/1999 | Delmore | A61L 15/30 602/76 |
| 6,258,196 | B1 * | 7/2001 | Suzuki | D04H 3/14 156/308.2 |
| 6,942,683 | B2 * | 9/2005 | Dunshee | A61F 13/0253 602/54 |
| 7,066,182 | B1 * | 6/2006 | Dunshee | A61B 17/085 602/41 |
| 8,642,735 | B2 * | 2/2014 | Murray | A61P 43/00 530/356 |
| 9,421,085 | B2 * | 8/2016 | Bindra | A61F 2/08 |
| 9,848,931 | B2 * | 12/2017 | Kartalian | A61B 17/88 |
| 10,080,644 | B2 * | 9/2018 | Goh | A61L 27/48 |
| 10,556,039 | B2 * | 2/2020 | Lynch | A61P 21/00 |
| 2002/0062114 | A1 * | 5/2002 | Murai | A61F 13/84 604/385.01 |
| 2003/0180570 | A1 * | 9/2003 | Cercone | E01F 9/696 428/626 |
| 2003/0229326 | A1 * | 12/2003 | Hovis | A61F 13/00995 604/370 |
| 2005/0136773 | A1 * | 6/2005 | Yahiaoui | D06M 15/03 442/394 |
| 2007/0207186 | A1 * | 9/2007 | Scanlon | B29C 55/26 623/1.42 |
| 2009/0060961 | A1 * | 3/2009 | Naruse | C08J 9/36 428/401 |
| 2009/0238849 | A1 * | 9/2009 | Iwata | A45D 44/002 424/443 |
| 2009/0292321 | A1 * | 11/2009 | Collette | A61F 2/0811 606/232 |
| 2010/0035500 | A1 * | 2/2010 | Kimura | D04H 1/50 28/103 |
| 2010/0063599 | A1 * | 3/2010 | Brunelle | A61B 17/06166 623/23.72 |
| 2012/0071975 | A1 * | 3/2012 | Gonzalez-Hernandez | A61B 17/1146 623/13.11 |
| 2012/0150078 | A1 * | 6/2012 | Chen | A61L 15/44 602/44 |
| 2012/0226296 | A1 * | 9/2012 | Bindra | A61B 17/1146 606/151 |
| 2013/0013065 | A1 * | 1/2013 | Bills | A61B 17/1146 623/13.15 |
| 2013/0122773 | A1 * | 5/2013 | Wahal | B29C 48/12 264/210.8 |
| 2014/0163586 | A1 * | 6/2014 | Holt | A61B 17/083 606/151 |
| 2016/0000490 | A1 * | 1/2016 | Kartalian | A61B 17/82 606/301 |
| 2016/0089257 | A1 * | 3/2016 | Meade | A61F 2/91 604/8 |
| 2016/0157992 | A1 * | 6/2016 | Goh | A61L 27/48 29/428 |
| 2016/0228608 | A1 * | 8/2016 | Hakimi | A61L 27/18 |
| 2018/0271670 | A1 * | 9/2018 | Diwan | A61F 2/442 |
| 2018/0344533 | A1 * | 12/2018 | Rovaniemi | A61F 13/0243 |
| 2020/0214691 | A1 | 7/2020 | Astorino | A61B 17/06166 |
| 2021/0338414 | A1 * | 11/2021 | Huang | A61H 1/00 |
| 2022/0054133 | A1 * | 2/2022 | Holt | A61B 17/083 |

FOREIGN PATENT DOCUMENTS

| | | |
|---|---|---|
| CN | 109689121 A | 4/2019 |
| CN | 110693629 A | 1/2020 |
| CN | 110740692 A | 1/2020 |
| CN | 111050677 A | 4/2020 |
| WO | WO 2016/113142 A1 | 7/2016 |

* cited by examiner

TISSUE REPAIR DEVICE AND METHOD FOR USING THE SAME

This application claims the benefit of Taiwan application Serial No. 109114515, filed Apr. 30, 2020, and Taiwan application Serial No. 110115426, filed Apr. 28, 2021, the disclosures of which are incorporated by reference herein in its entirety.

TECHNICAL FIELD

The technical field relates to tissue repair device and method for using the same.

BACKGROUND

Recently, the exercise has become more and more popular, and good habits in health are beneficial for the health. However, too high exercise intensity, carelessness during exercise, etc. may cause injury to body tissues. For example, too vigorous and prolonged exercise may cause damage to the anterior cruciate ligament of the knee joint. Although there are currently clinical reconstruction operations for the cruciate ligament, due to insufficient local blood volume, it is unable to effectively provide nutrients, and the enzymes in the joint capsule interfere with the repair, so the failure rate of the operation is high (more than 50%).

Therefore, there is an urgent need to develop a device or method that can improve tissue repair to solve the conventional problems.

SUMMARY

According to one embodiment, a tissue repair device is provided. The tissue repair device includes a body portion and at least one wire. The body portion includes an inner layer and an outer layer. The inner layer is close to a tissue, wherein the inner layer includes a hydrophilic structure, and the outer layer includes a hydrophobic structure. The wire is connected to the body portion to fix the body portion to the tissue.

According to another embodiment, a method for using a tissue repair device is provided. The method includes the following steps. Firstly, the tissue repair device is approached toward an injured position of a tissue, so that a body portion of the repair device surrounds the injured position of the tissue. Then, the body portion of the repair device is fixed to the tissue with suture(s) and/or wire(s), so that an inner layer of the body portion of the tissue repair device surrounds the injured position to form a closed accommodating space, which is separated from external space. After that, a repairing liquid is injected the inner layer of the accommodating space to help with infiltration and repair of the tissue.

In order to have a better understanding of the above-mentioned and other aspects of the present disclosure, the following embodiments are specially cited, and the accompanying drawings are described in detail as follows:

DETAILED DESCRIPTION

The present disclosure relates to a tissue repair device. Since an inner layer of the tissue repair device is closer to the tissue than an outer layer of the tissue repair device, and the inner layer includes a hydrophilic structure, it can retain repair fluid (such as blood, gel and other biologically functional substances) near an injured position of the tissue to assist tissue repair. The outer layer includes a hydrophobic structure, which can form a protective layer to prevent the enzymes in the joint fluid from directly acting on the injured position of the tissue and inhibiting the repair of the tissue. Therefore, the tissue repair device of the present disclosure can improve the repair condition of the tissue.

Figure 1A:
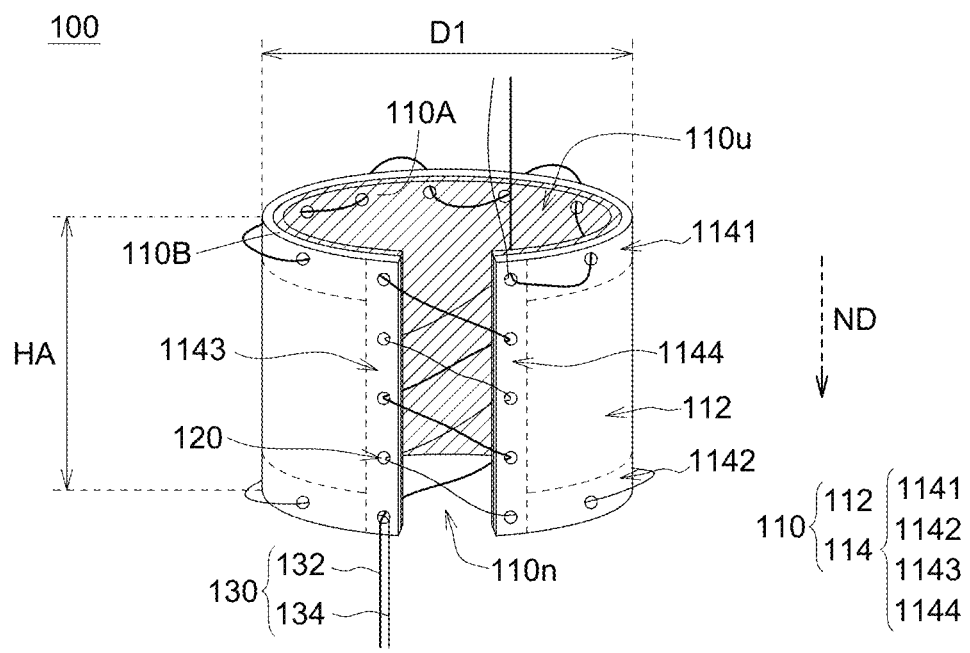
FIG. 1A shows a three-dimensional view of a tissue repair device of the present disclosure when a wire is not yet tightened.
Figure 1B:
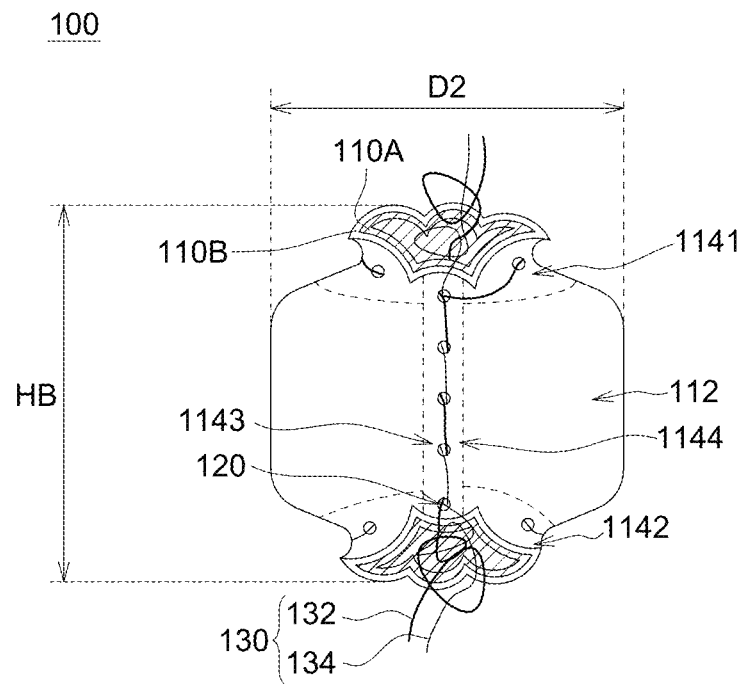
FIG. 1B shows a side view of a tissue repair device of the present disclosure after a wire is tightened.

FIG. 1A shows a perspective view of a tissue repair device 100 according to an embodiment of the present invention when a wire 130 is not yet tightened. FIG. 1B shows a side view of the tissue repair device 100 after the wire 130 is tightened according to an embodiment of the present disclosure. In the tissue repair device 100, when the wire 130 is not tightened, it indicates that the tissue repair device 100 has not been fixed on the tissue. In the tissue repair device 100, after the wire 130 has been tightened, it indicates that the tissue repair device 100 has been fixed on the tissue. FIGS. 2A to 2D show schematic diagrams of a method for using the tissue repair device 100 according to an embodiment of the present disclosure. FIGS. 3A to 3D show cross-sectional views of fibers in the hydrophilic fabric of the tissue repair device 100 according to some embodiments of the present disclosure.

Refer to FIGS. 1A and 1B at the same time. The tissue repair device 100 includes a body portion 110 and a wire 130. The body portion 110 includes an inner layer 110A and an outer layer 110B. The inner layer 110A is closer to a tissue (such as the anterior cruciate ligament Lg shown in FIGS. 2A-2D) than the outer layer 110B, wherein the inner layer 110A includes a hydrophilic structure, and the outer layer 110B includes a hydrophobic structure. The body portion 110 includes an upper opening 110u and a lower opening 110n communicating with each other. Therefore, the body portion 110 has a space corresponding to an injured position of the tissue, so that the body portion 110 can surround the injured position of the tissue.

In one embodiment, the body portion 110 includes a middle portion 112, an edge portion 114, and a plurality of holes 120. The edge portion 114 is connected to the middle portion 112, and the edge portion 114 includes a first edge portion 1141, a second edge portion 1142, a third edge portion 1143, and a fourth edge portion 1144. The first edge portion 1141 corresponds to the upper opening 110u, the second edge portion 1142 corresponds to the lower opening 110n, the third edge portion 1143 and the fourth edge portion 1144 are connected to the first edge portion 1141 and the second edge portion 1142. The third edge portion 1143 is opposite to the fourth edge portion 1144 (that is, disposed on opposite sides of the first edge portion 1141 and the second edge portion 1142). The third edge portion 1143 and the fourth edge portion 1144 are not directly connected. When the wire 130 is not tightened, the third edge portion 1143 and the fourth edge portion 1144 are separated from each other, and there may be a gap between them, as shown in FIG. 1A. For example, when the wire 130 is not tightened, the extension directions of the first edge portion 1141 and the second edge portion 1142 are parallel to each other, forming an arc-shaped structure, respectively, and the extension directions of the third edge portion 1143 and the fourth edge portion 1144 are parallel to a first direction ND. The first direction ND is, for example, a direction extending from the upper opening 110u toward the lower opening 110n, but the present disclosure is not limited thereto. After the wire 130 is tightened, the third edge portion 1143 and the fourth edge portion 1144 are close to each other, for example, overlap each other, and the first edge portion 1141 and the second edge portion 1142 are both tightened to close the upper opening 110u and the lower opening 110n, respectively. In some embodiments, before the wire 130 is tightened, the first diameter D1 of the tissue repair device 100 is, for example, between 15 mm and 35 mm, as shown in FIG. 1A; after the wire 130 is tightened, the second diameter D2 of the tissue repair device 100 is reduced, for example, between 5 mm and 15 mm, as shown in FIG. 1B. Before and after the wire 130 is tightened, the first height HA and the second height HB of the tissue repair device 100 may be the same or similar, for example, between 15 mm and 25 mm, as shown in FIGS. 1A and 1B. The first diameter D1 and the second diameter D2 of the tissue repair device 100 are, for example, the largest diameters formed by the middle portion 112 of the body portion 110 of the tissue repair device 100.

A plurality of holes 120 are disposed in the edge portion 114 of the body portion 110. The plurality of holes 120 are disposed in the first edge portion 1141, the second edge portion 1142, the third edge portion 1143, and the fourth edge portion 1144 and are separated from each other, respectively. The holes 120 penetrate the edge portion 114 of the body portion 110 (that is, penetrate the inner layer 110A and the outer layer 110B) to provide a threading path of the wire 130. In some embodiments, the holes 120 may have the same spacing, but the present disclosure is not limited thereto, and the spacing between the holes 120 may also be different, which can be adjusted according to requirements.

In the present embodiment, the wire 130 includes a first wire 132 and a second wire 134. The first wire 132 and the second wire 134 pass through the holes 120 to be detachably connected to the body portion 110. That is, the first wire 132 passes through a portion of the holes 120, and the second wire 134 passes through another portion of the holes 120, and after the injured position (for example, the injured position IP shown in FIG. 2A) is surrounded by the body portion 110 by tightening the first wire 132 and the second wire 134 such that the first edge portion 1141 and the second edge portion 1142 are approached toward the tissue (for example, the anterior cruciate ligament Lg shown in FIGS. 2A to 2D), so that the body portion 110 is fixed to the tissue (for example, the anterior cruciate ligament Lg shown in FIGS. 2A to 2D).

For example, as shown in FIG. 1A, after passing through the uppermost hole 120 of the fourth edge portion 1144, the first wire 132 sequentially shuttles through the holes 120 of the first edge portion 1141. After passing through the uppermost hole 120 in the third edge portion 1143, the first wire 132 alternately shuttles down between the third edge portion 1143 and the fourth edge portion 1144, and then passing through the lowermost hole 120 of the third edge portion 1143 to the outside. After the second wire 134 passes through the uppermost hole 120 of the fourth edge portion 1144 to the inside, the second wire 134 shuttles down alternately between the third edge portion 1143 and the fourth edge portion 1144, and then sequentially shuttles through the holes 120 of the second edge portion 1142, thereafter, the second wire 134 passes through the lowermost hole 120 of the third edge portion 1143 to the outside. However, the method for the first wire 132 and the second wire 134 to shuttle through the holes 120 is not limited thereto. The first wire 132 and the second wire 134 are shown as lines with different thicknesses to distinguish the first wire 132 and the second wire 134 from each other, but the present disclosure is not limited thereto, the thickness of the first wire 132 and the second wire 134 may be the same or different.

In some embodiments, the inner layer 110A and the outer layer 110B may be bonded by an adhesive, or combined with each other by stitching. However, the present disclosure is not limited thereto, as long as the inner layer 110A and the outer layer 110B can be attached to each other.

Figure 2D:
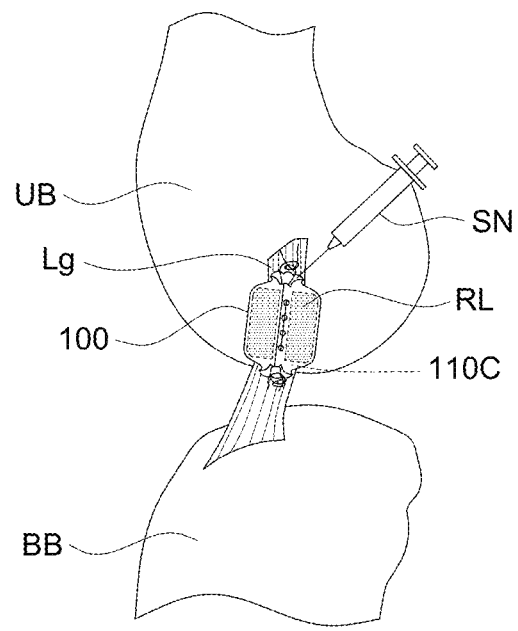
Figure 3A:
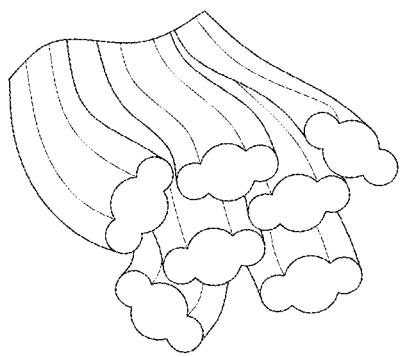
FIGS. 3A~3D show the cross-sections of fibers in the hydrophilic fabric of the tissue repair device of the present disclosure.
Figure 3B:
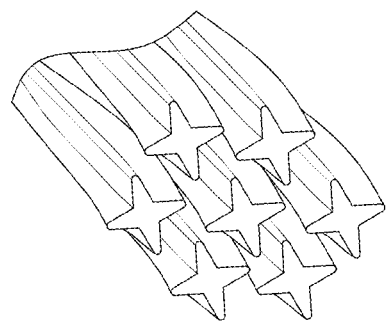
Figure 3C:
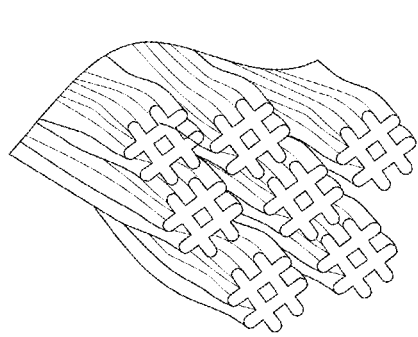
Figure 3D:
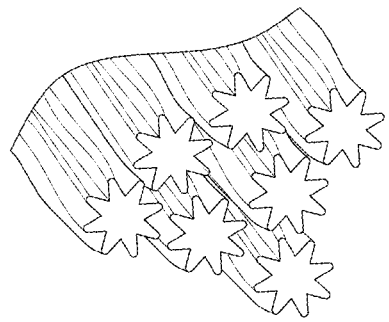

In some embodiments, the hydrophilic structure of the inner layer 110A includes a hydrophilic fabric, and the material of the hydrophilic fabric may include polyethyleneterephthalate (PET), poly lactic acid (PLA), Polyethylene naphthalate (PEN), or a combination thereof. Polyethyleneterephthalate and poly lactic acid can be made into fiber materials, respectively, that is, polyethyleneterephthalate and poly lactic acid may be made into polyethyleneterephthalate fiber and poly lactic acid fibers, respectively. The polyethyleneterephthalate fiber, the poly lactic acid fiber and the fiber of the combination thereof may be woven into "polyethyleneterephthalate fiber fabric", "poly lactic acid fiber fabric" and "polyethyleneterephthalate fiber and poly lactic acid fiber fabric", respectively. In other words, the hydrophilic fabric includes the polyethyleneterephthalate fiber, the poly lactic acid fiber and a combination thereof. The fiber of the hydrophilic fabric is non-cylindrical, and its cross-section is, for example, non-circular, such as butterfly-shaped (as shown in FIG. 3A), cross-shaped (as shown in FIG. 3B), pound sign-shaped with hollow holes (as shown in FIG. 3C), eight-pointed star-shaped (as shown in FIG. 3D). Since the cross-section of the fiber of the hydrophilic fabric is non-circular, it allows water to flow through the pores between the fibers, so it can quickly absorb water. However, the non-cylindrical shape of the present disclosure is not limited thereto, as long as it can achieve the function of rapid water absorption, it can be the scope protected by the present disclosure. Therefore, in the present application, through the design that the inner layer 110A of the tissue repair device 100 includes a hydrophilic structure, it can achieve the function of rapid water absorption, and can also quickly absorb the injected repair liquid (as shown in FIG. 2D).

In some embodiments, the hydrophobic structure of the outer layer 110B includes a hydrophobic fabric, and the hydrophobic fabric includes the polyethyleneterephthalate fiber, the poly lactic acid fiber, or a combination thereof. In some embodiments, the density of the hydrophobic fabric fibers is between 2,000 and 12,000. The fiber density herein is referred to the CF value, which is calculated by the following Formula 1:

$$CF = (DWp/1.1)^{1/2} \times MWp + (DWf/1.1)^{1/2} \times MWf \quad \text{(Formula 1)}$$

Wherein DWp represents the total deny number of warp yarns; MWp represents the density of warp yarns, that is, the number of warp yarns per 2.54 cm; DWf represents the total deny number of weft yarns; MWf represents the density of weft yarns, that is, the number of weft yarns per 2.54 cm. In some embodiments, the fineness of the hydrophobic fabric fiber is between 0.00002 dtex and 0.022 dtex. In some embodiments, the thickness of the hydrophobic fabric is between 0.05 mm and 0.25 mm. The diameter and density of the fiber will affect the thickness of the material structure. If it is too thick, it will be disadvantageous for minimally invasive surgery. Since the tissue repair device 100 of the present disclosure has a design that the outer layer 110B includes a hydrophobic structure, substances that are not beneficial to tissue repair can be prevented from entering the injured position of the tissue, so that the condition of the tissue repair is improved. Among them, substances that are not beneficial to the tissue repair are, for example, environmental enzymes (for example, urokinase-type plasminogen activator (uPA) in synovial fluid).

In some embodiments, the wire 130 may be a general surgical suture, such as silk thread, prolene, Vicryl Rapide, Vicryl, Monocryl, Dexon, PDS II or other surgical sutures, but the present disclosure is not limited thereto. Both absorbable surgical sutures or non-absorbable surgical sutures can be used as the wire 130 in the present disclosure. In some embodiments, the material of the wire 130 may also be polyethyleneterephthalate fiber, polylactic acid fiber, or a combination of the foregoing.

FIG. 10 shows a side view of the tissue repair device 100' according to another embodiment of the present disclosure when the wire 130 is not tightened. The tissue repair device 100' is similar to the tissue repair device 100, and the difference is in that the ways of the first wire 132 and the second wire 134 passing through the holes 120 are different, and other similarities will not be repeated. For example, after passing through the uppermost hole 120 in the third edge portion 1143, the first wire 132 may sequentially pass through the holes 120 in the first edge portion 1141, and then, after passing through the uppermost hole 120 in the fourth edge portion 1144, alternately shuttles down between the third edge portion 1143 and the fourth edge portion 1144, and then passes through the lowermost hole 120 of the fourth edge portion 1144. After the second wire 134 passes through the uppermost hole 120 in the fourth edge portion 1144 to the inside, the second wire 134 passes through the uppermost hole 120 in the third edge portion 1143, and then alternately shuttles down the fourth edge portion 1144 and the third edge portion 1143, and after passing through the lowermost hole 120 of the third edge part 1143, sequentially shuttles through the holes 120 of the second edge portion 1142, and then passes through the lowermost hole 120 of the third edge portion 1143 to the outside.

In the past clinical studies, it has been found that due to insufficient local blood volume in the injured tissue, it cannot effectively provide nutrients, and there are enzymes in the joint capsule that inhibit tissue repair, which makes it difficult to repair ligament damage or tendon damage, and the failure rate of surgery is high. By arranging the tissue repair device 100 or 100' according to an embodiment of the present disclosure at the injured position of the tissue, on the one hand, the hydrophilic structure of the inner layer 110A can retain blood volume, and on the other hand, the hydrophobic structure of the outer layer 110B can be used for blocking enzymes which interferes with tissue repair, so it can improve tissue repair. Furthermore, the tissue repair device 100 or 100' of the present disclosure is easy to operate, and can be easily fixed to the injured position of the tissue, and is suitable for minimally invasive surgery, arthroscopic operation or other surgical operations, which can save the time spent on surgery, such that the success rate of surgery is greatly improved.

FIGS. 2A to 2D illustrate the ligaments of the knee joint, for example, the anterior cruciate ligament Lg between the femur UB and the tibia BB, but the present disclosure is not limited thereto. The tissue repair device disclosed in the present disclosure can be applied to repair ligaments, tendons and other suitable tissues.

Figure 2A:
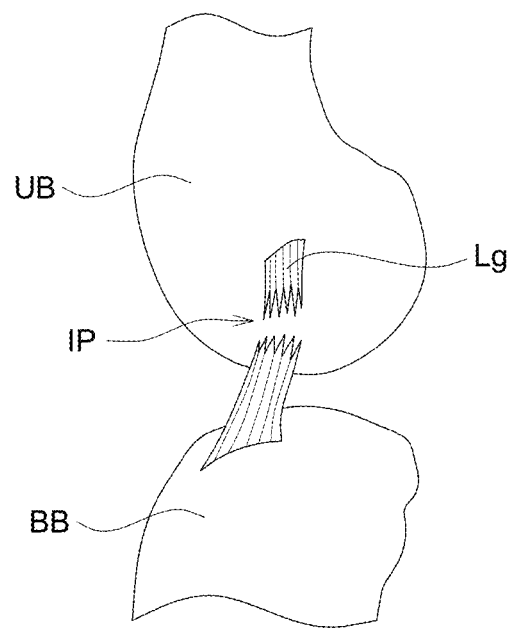
FIGS. 2A~2D show schematic diagrams of a method for using the tissue repair device of the present disclosure.

First, referring to FIG. 2A, which shows the anterior cruciate ligament Lg between the femur UB and the tibia BB, and the anterior cruciate ligament Lg has an injured position IP.

Figure 2B:
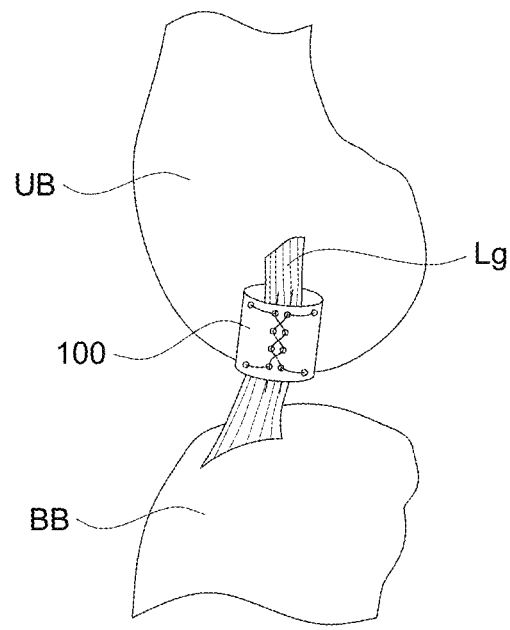

Next, referring to FIG. 2B, the tissue repair device 100 (for example, the tissue repair device 100 shown in FIGS. 1A to 1B) is approached toward the injured position IP of the tissue (for example, the anterior cruciate ligament Lg), and the injured position IP of the tissue (for example, the anterior cruciate ligament Lg) is surrounded by the body portion 110 of the tissue repair device 100.

Figure 2C:
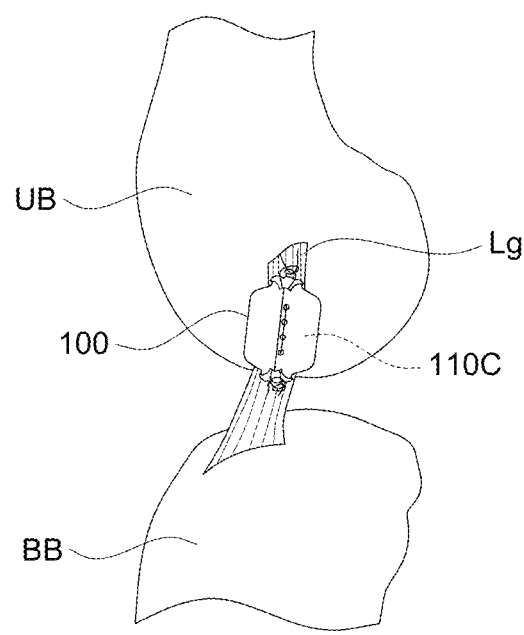

Then, referring to FIG. 2C, the body portion 110 is fixed to the tissue (for example, the anterior cruciate ligament Lg) by the wire 130 of the tissue repair device 100, and the inner layer 110A surrounds the injured position IP to form an accommodating space 110C.

After that, referring to FIG. 2D, a repair liquid RL (such as, blood, gel, growth factor, and other biologically functional substances) is injected into the accommodating space 110C of the inner layer 110A through an injection syringe SN, to assists in repairing the tissue (for example, the anterior cruciate ligament Lg). Since the inner layer 110A includes a hydrophilic structure, and the wire 130 can close the upper opening 110u and the lower opening 110n of the body portion 110, the accommodating space 110C formed by the inner layer 110A is, for example, a nearly-closed chamber, which can make the most portion of the liquid remained in the accommodating space 110C to avoid flowing to the outside.

Figure 1C:
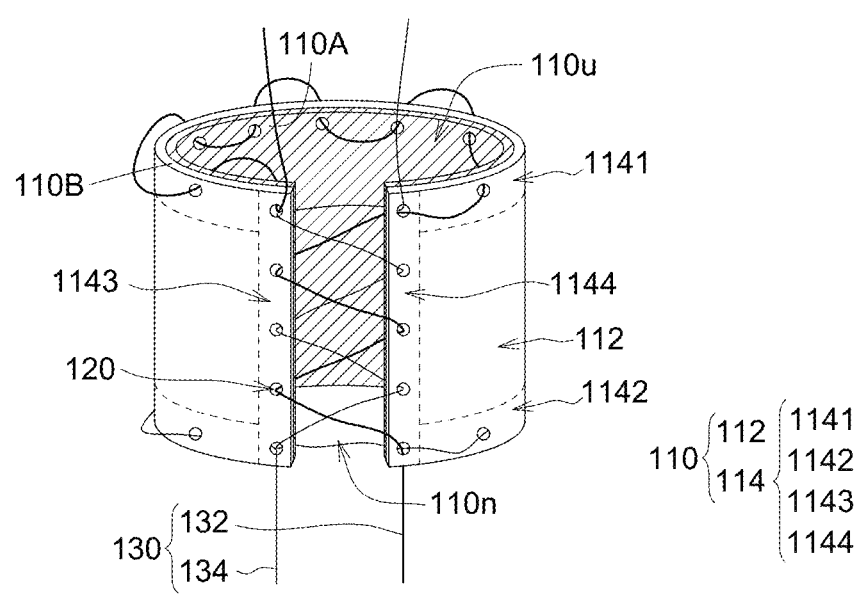
FIG. 1C shows a side view of a tissue repair device of the present disclosure when a wire is not yet tightened.

FIGS. 2B~2D exemplarily show an embodiment of using the tissue repair device 100, but the present disclosure is not limited thereto. The tissue repair device 100' shown in FIG. 1C, the tissue repair device 200 shown in FIGS. 4A-4D, the tissue repair device 200' shown in FIG. 4E, the tissue repair device 300 shown in FIGS. 5A-5B, or any tissue repair device in the scope of the present disclosure can also be used.

Figure 4A:
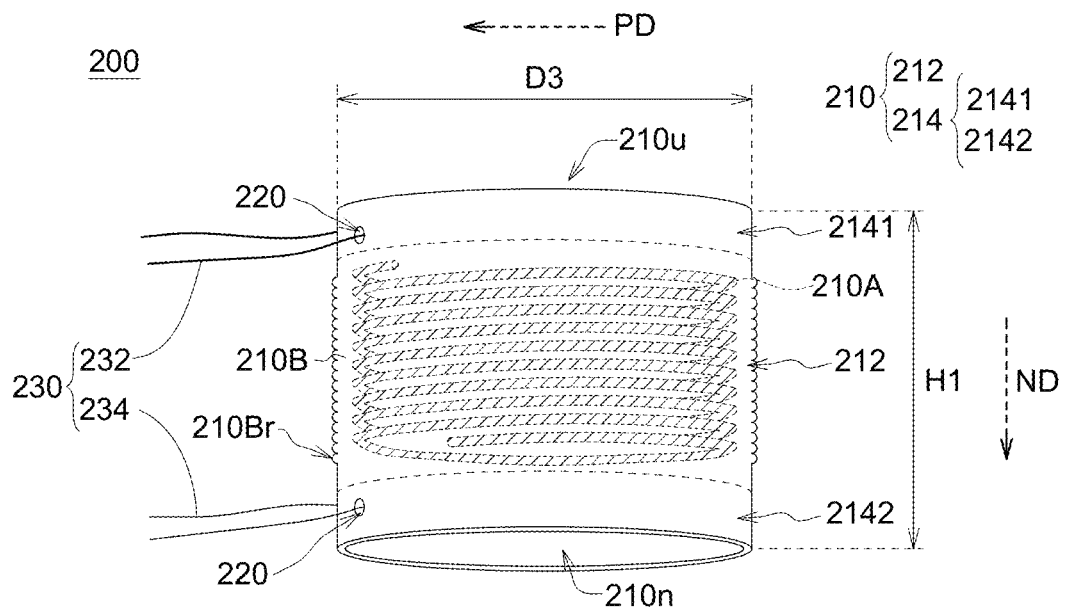
FIG. 4A shows a three-dimensional view of a tissue repair device of the present disclosure when a wire is not yet tightened.
Figure 4B:
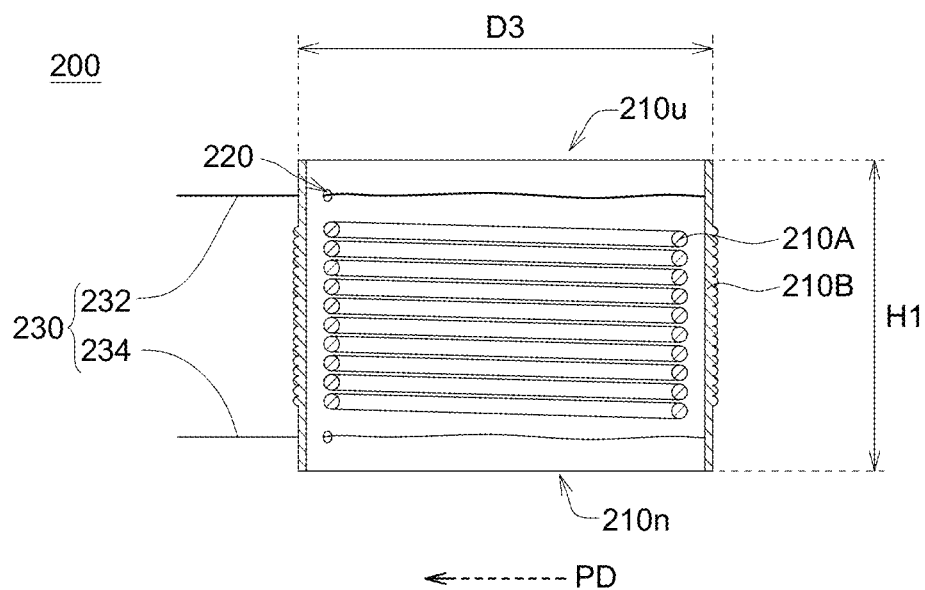
FIG. 4B shows a cross-sectional view of FIG. 4A.
Figure 4C:
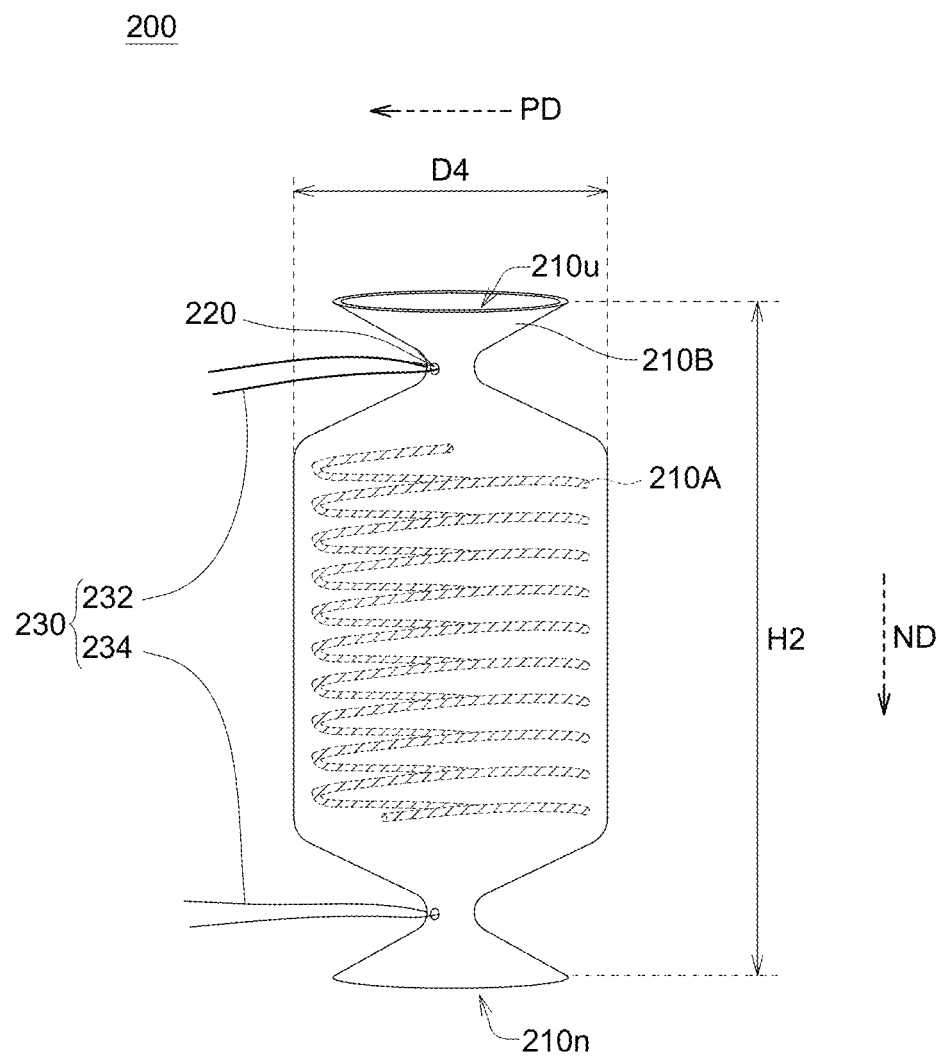
FIG. 4C shows a three-dimensional view of a tissue repair device of the present disclosure after a wire is tightened.
Figure 4D:
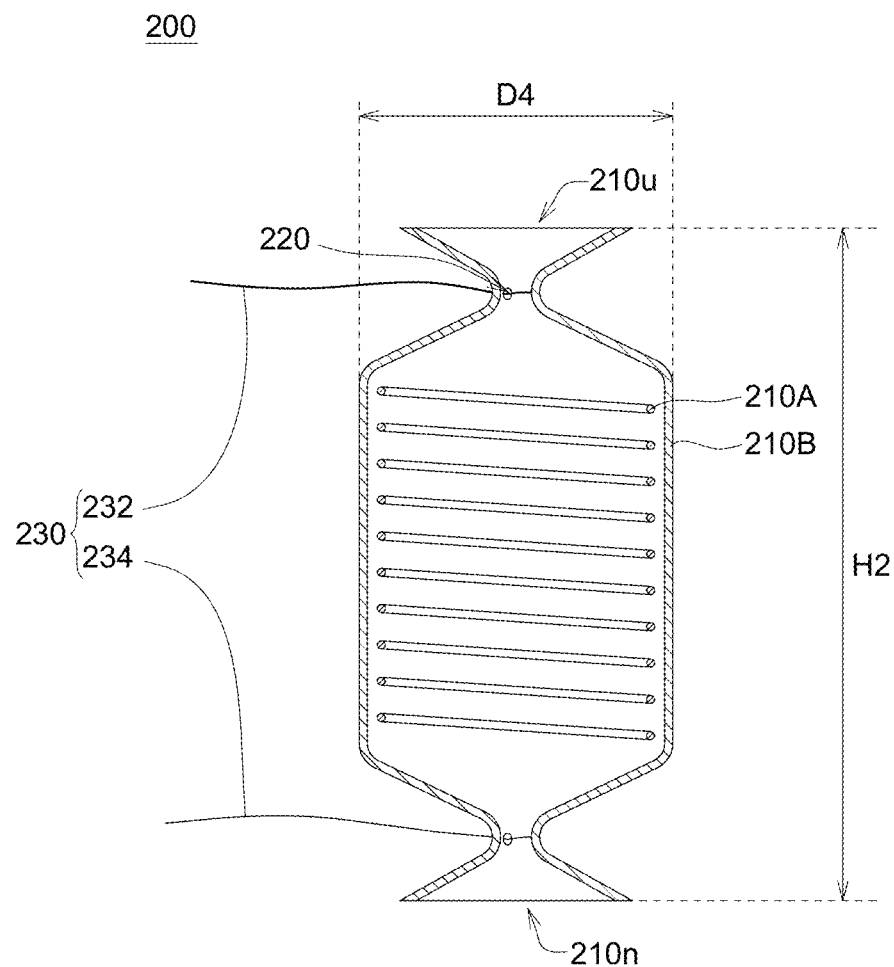
FIG. 4D shows a cross-sectional view of FIG. 4C.

FIG. 4A shows a perspective view of the tissue repair device 200 according to an embodiment of the present invention when the wire 230 has not been tightened. FIG. 4B shows a cross-sectional view of FIG. 4A. FIG. 4C shows a perspective view of a tissue repair device 200 according to an embodiment of the present disclosure after the wire 230 is tightened. FIG. 4D shows a cross-sectional view of FIG. 4C.

Referring to FIGS. 4A and 4B at the same time, the tissue repair device 200 includes a body portion 210 and a wire 230. The body portion 210 includes an inner layer 210A and an outer layer 210B. The inner layer 210A is closer to a tissue (for example, the anterior cruciate ligament Lg shown in FIGS. 2A-2D) than the outer layer 210B, wherein the inner layer 210A includes a hydrophilic structure, the outer layer 210B includes a hydrophobic structure. The body portion 210 includes an upper opening 210u and a lower opening 210n communicating with each other. Therefore, the body portion 210 has a space corresponding to the injured position of the tissue, so that the body portion 210 can surround the injured position of the tissue.

The hydrophilic structure of the inner layer 210A, the hydrophobic structure of the outer layer 210B, and the materials and properties of the wire 230 of the tissue repair device 200 are respectively the same or similar to the hydrophilic structure of the inner layer 110A, the hydrophobic structure of the outer layer 110B, and the materials and properties of the wire 130 of the tissue repair device 100, the similarities will not be repeated.

In one embodiment, the body portion 210 includes a middle portion 212, an edge portion 214, and a plurality of holes 220. The edge portion 214 is connected to the middle portion 212, and the edge portion 214 includes a first edge portion 2141 and a second edge portion 2142. The first edge portion 2141 corresponds to the upper opening 210u, and the second edge portion 2142 corresponds to the lower opening 210n.

A plurality of holes 220 are disposed in the edge portion 214 of the body portion 210 to provide a threading path of the wire 230. For example, the first edge portion 2141 has two holes 220 that are adjacent and separated from each other, and the two holes 220 of the first edge portion 2141 are communicated with each other through, for example, a threading channel (not shown). The threading channel (not shown) of the first edge portion 2141 is, for example, disposed between the outer surface of the outer layer 210B and the inner surface of the inner layer 210A, and surrounds the upper opening 210u along the first edge portion 2141. The second edge portion 2142 has two holes 220 that are adjacent and separated from each other, and the two holes 220 of the second edge portion 2142 are communicated with each other through, for example, a threading channel (not shown). The threading channel (not shown) of the second edge portion 2142 is, for example, disposed between the outer surface of the outer layer 210B and the inner surface of the inner layer 210A, and surrounds the lower opening 210n along the second edge portion 2142. However, the number of holes 220 is not limited thereto. In some embodiments, the holes 220 may penetrate the inner layer 210A and the outer layer 210B at the same time, or the holes 220 may only penetrate the inner layer 210A or only penetrate the outer layer 210B. However, the present disclosure is not limited thereto.

The wire 230 includes a first wire 232 and a second wire 234, and the first wire 232 passes through two holes 220 formed in the first edge portion 2141. For example, after the first wire 232 passes through one of the holes 220 of the first edge portion 2141, the first wire 232 surrounds the upper opening 210u along the threading channel (not shown) of the first edge portion 2141, and then passes through another hole 220 of the first edge portion 2141 to the outside. The second wire 234 passes through two holes 220 disposed in the second edge portion 2142. For example, after the second wire 234 passes through one of the holes 220 of the second edge portion 2142, the second wire 234 surrounds the lower opening 210n along the threading channel (not shown) of the second edge portion 2142, and then passes through another hole 220 of the second edge portion 2142 to the outside. However, the arrangement relationship between the wire 230 and the hole 220 in an embodiment of the present disclosure is not limited thereto, and the arrangement between the wire 130 and the hole 120 can also be used in any combination with the arrangement between the wire 230 and the hole 220, as long as the tissue repair device 100 or 200 can be fixed on the tissue.

In some embodiments, the outer layer 210B is a hollow cylindrical structure, the inner layer 210A is a spiral structure, and the inner layer 210A extends in a spiral manner from the upper opening 210u to the lower opening 210n in the middle portion 212.

In some embodiments, a height of the body portion 210 in a first direction ND is adjustable, and the first direction ND is parallel to the direction extending from the upper opening 210u to the lower opening 210n. Before the body portion 210 surrounds the injured position (for example, the injured position IP shown in FIG. 2A), the body portion 210 has a first height H1 in the first direction ND, as shown in FIGS. 4A to 4B. After the body portion 210 is fixed on the tissue, the body portion 210 has a second height H2 in the first direction ND, and the second height H2 is greater than the first height H1, as shown in FIGS. 4C-4D. Before the body portion 210 surrounds the injured position (for example, the injured position IP shown in FIG. 2A), the body portion 210 has a first diameter D3 in the second direction PD, as shown in FIGS. 4A-4B. After the body portion 210 is fixed on the tissue, the body portion 210 has a second diameter D4 in the second direction PD, and the first diameter D3 is larger than the second diameter D4, as shown in FIGS. 4C~4D. The second direction PD is, for example, perpendicular to the first direction ND. In some embodiments, the first height H1 is, for example, between 5 mm and 25 mm, the second height H2 is, for example, between 15 mm and 50 mm; the first diameter D3 is, for example, between 15 mm and 35 mm, and the second diameter D4 is, for example, between 5 mm and 15 mm.

Before the body portion 210 surrounds the injured position (for example, the injured position IP shown in FIG. 2A), the spiral inner layer 210A has a smaller space in the first direction ND, and the outer layer 210B has some wrinkled portions 210Br corresponding to the inner layer 210A, these wrinkled portions provide a space for the body portion 210 to be stretched later.

After the body portion 210 surrounds the injured position (for example, the injured position IP shown in FIG. 2A), the body portion 210 is pulled up and down to be higher, that is, the spiral inner layer 210A has larger spaces in the first direction ND, the wrinkled portion of the outer layer 210B is flattened to form a hollow cylindrical structure. Thereafter, by tightening the first wire 232 and the second wire 234, the first edge portion 2141 and the second edge portion 2142 are approached toward the tissue (for example, the anterior cruciate ligament Lg shown in FIGS. 2A to 2D), so that the body portion 210 is fixed on the tissue.

Figure 4E:
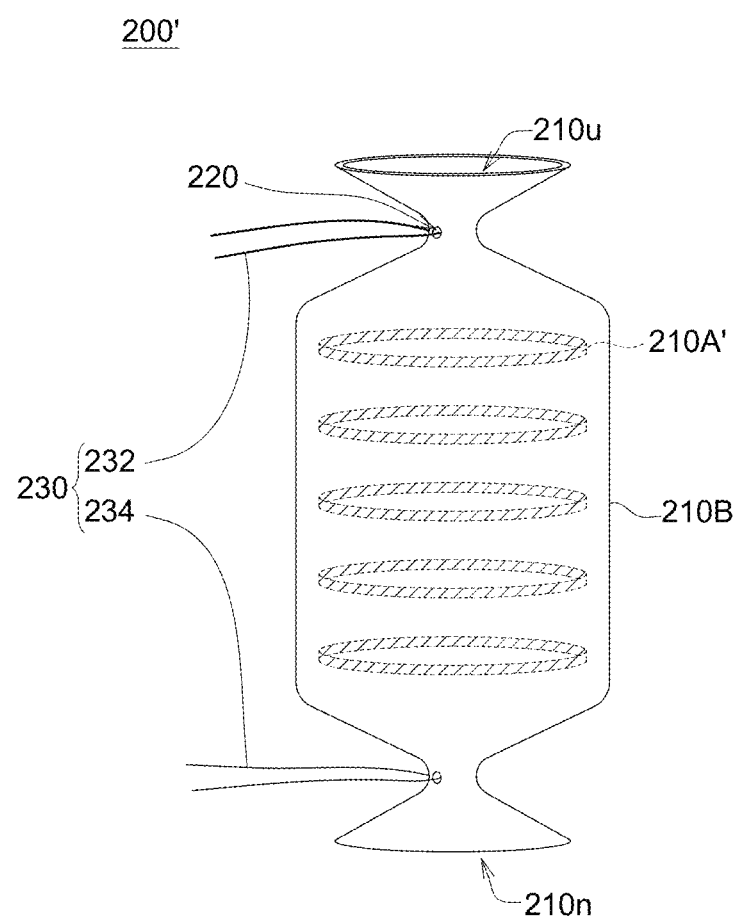
FIG. 4E shows a three-dimensional view of a tissue repair device of the present disclosure after a wire is tightened.

FIG. 4E shows a three-dimensional view of the tissue repair device 200' according to another embodiment of the present disclosure after the wire 230 is tightened. The tissue repair device 200' is similar to the tissue repair device 200, except that the design of the inner layer 210A' of the tissue repair device 200' is different, and the other identical parts will not be described again.

Referring to FIG. 4E, the outer layer 210B is a hollow cylindrical structure, and the inner layer 210A includes a plurality of ring structures, which are separated from each other and are disposed along the extending direction (for example, the first direction ND) from the upper opening 210u to the lower opening 210n in the middle portion 212. Similar to the tissue repair device 200, the height of the body portion 210 of the tissue repair device 200' in a first direction ND is adjustable (for example, the first height H1 is smaller than the second height H2), and before and after the wire 230 is tightened, the diameter of the body portion 210 in the second direction PD also changes (for example, the first diameter D1 is greater than the second diameter D2), and the similarities will not be described again.

Since the height of the tissue repair devices 200 and 200' in the first direction ND is adjustable, compared with the comparative example where the height in the first direction ND is not adjustable, the tissue repair devices 200 and 200' can have a smaller height before surrounding the tissue, which is easier to place on the injured position of the tissue, and can improve the convenience of the operation. In addition, the spiral or multi-ring design of the inner layer 210A in the tissue repair devices 200 and 200' facilitates the compression and expansion of the body portion 210.

By arranging the tissue repair device 200 or 200' of an embodiment of the present disclosure at the injured position of the tissue, on the one hand, the hydrophilic structure of the inner layer 210A can retain blood volume, and on the other hand, the hydrophobic structure of the outer layer 210B can block enzymes from interfering with the tissue repair, so it can improve tissue repair. Furthermore, the tissue repair device 200 or 200' of the present embodiment is easy to operate and can be easily fixed to the injured position of the tissue. It is suitable for minimally invasive surgery, arthroscopic operation or other surgical operations, such that the success rate of surgery may be increased significantly.

Figure 5A:
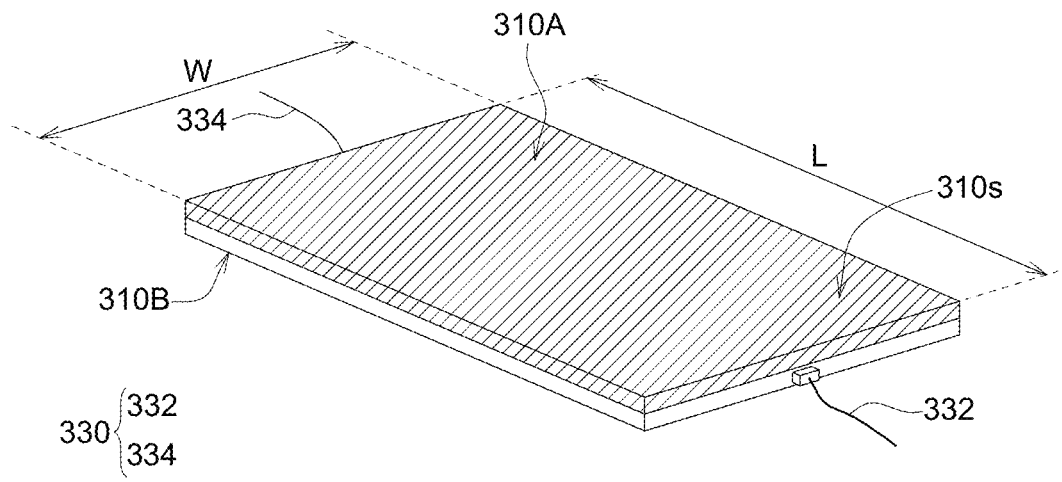
FIG. 5A shows a three-dimensional view of a tissue repair device of the present disclosure before surrounding the tissue.
Figure 5B:
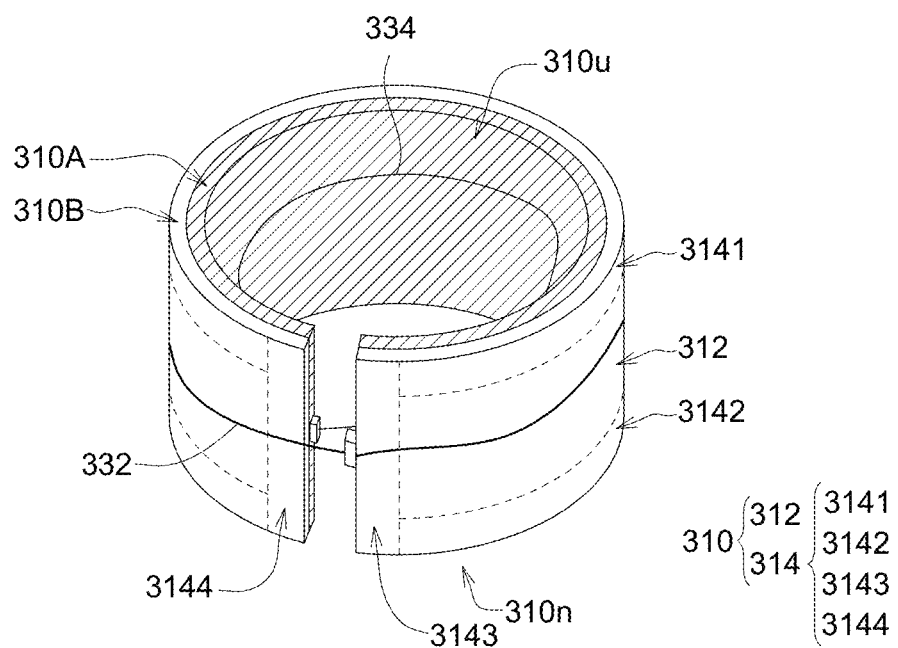
FIG. 5B shows a three-dimensional view of a tissue repair device of the present disclosure after surrounding the tissue.

FIG. 5A shows a three-dimensional view of the tissue repair device 300 before surrounding the tissue according to an embodiment of the present disclosure. FIG. 5B is a three-dimensional view of the tissue repair device 300 after surrounding the tissue according to an embodiment of the present disclosure.

Referring to FIGS. 5A and 5B at the same time, the tissue repair device 300 includes a body portion 310 and a wire 330. The body portion 310 includes an inner layer 310A and an outer layer 310B. The inner layer 310A is closer to a tissue (for example, the anterior cruciate ligament Lg shown in FIGS. 2A-2D) than the outer layer 310B, wherein the inner layer 310A includes a hydrophilic structure, and the outer layer 310B includes a hydrophobic structure. The body portion 310 is configured to surround an injured position of the tissue. Before the body portion 310 surrounds the injured position, the body portion 310 has a sheet structure, as shown in FIG. 5A. After the body portion 310 surrounds the injured position, the body portion 310 has a hollow cylindrical structure, as shown in FIG. 5B. For example, the tissue repair device 300 directly covers and winds around the injured position of the tissue.

The tissue repair device 300 includes a middle portion 312 and an edge portion 314. The edge portion 314 is connected to the middle portion 312, and the edge portion 314 includes a first edge portion 3141, a second edge portion 3142, a third edge portion 3143, and a fourth edge portion 3144. The first edge portion 3141 is opposite to the second edge portion 3142, and the third edge portion 3143 is opposite to the fourth edge portion 3144. In the present embodiment, the wire 330 includes a first wire 332 and a second wire 334, and the first wire 332 and the second wire 334 are connected to the third edge portion 3143 and the fourth edge portion 3144, respectively. However, the number of wires 330 of the present disclosure is not limited thereto, and the number of the wires 330 can be 3, 4 or other suitable numbers. The first wire 332 can be connected to the third edge portion 3143 or the fourth edge portion 3144; the second wire 334 can be connected to the third edge portion 3143 or the fourth edge portion 3144.

After the body portion 310 surrounds the injured position, the body portion 310 has an upper opening 310u and a lower opening 310n. The upper opening 310u communicates with the lower opening 310n, and the first edge portion 3141 corresponds to the upper opening 310u, the second edge portion 3142 corresponds to the lower opening 310n. After the body portion 310 surrounds the injured position, the wire 330 is wound on the outer layer 310B of the body portion 310 to fix the body portion 310 to the tissue. In the present embodiment, the first wire 332 can be used to bind or fix the tissue repair device 300 at the outer layer 310B, and the second wire 334 can be used to bind or fix the tissue at the inner layer 310A.

The materials and properties of the hydrophilic structure of the inner layer 310A, the hydrophobic structure of the outer layer 310B, and the wire 330 of the tissue repair device 300 are respectively identical or similar to the materials and properties of the hydrophilic structure of the inner layer 110A, the hydrophobic structure of the outer layer 110B, and the wire 130 of the tissue repair device 100, the similarities will not be described again.

As shown in FIG. 5A, when the tissue repair device 300 is a sheet structure, the length L of the tissue repair device 300 is, for example, between 15 mm and 45 mm; the width W of the tissue repair device 300 is, for example, between 5 mm and 15 mm. In the present embodiment, the edges of the inner layer 310A and the outer layer 310B can be aligned with each other in a normal direction of the inner surface 310s, but the present disclosure is not limited thereto. The edges of the inner layer 310A and the outer layer 310B may be separated from each other in a normal direction of the inner surface 310s.

By arranging the tissue repair device 300 of an embodiment of the present disclosure at the injured position of the tissue, on the one hand, the hydrophilic structure of the inner layer 310A can retain blood volume, and on the other hand, the hydrophobic structure of the outer layer 310B can block enzymes from interfering with the repair of the tissue, so the repair condition of the tissue can be improved. Furthermore, the tissue repair device 300 of the present disclosure is easy to operate and can be easily fixed to the injured position of the tissue. It is suitable for minimally invasive surgery, arthroscopic operation or other surgical operations, which can save the time spent on the operation and significantly increase the success rate of the operation.

EXAMPLES

Test for Hydrophilic Fabric and Hydrophobic Fabric

In order to verify that the inner layer and the outer layer of the tissue repair device of the present disclosure have different hydrophilic and hydrophobic properties, and can respectively achieve the functions of retaining biologically active factors such as blood and isolating enzymes, the following will conduct a water content test.

Example 1

In the present disclosure, hydrophobic fabric EF1 and hydrophilic fabric EF2 were used for water content tests. The materials of hydrophobic fabric EF1 and hydrophilic fabric EF2 were all polyethyleneterephthalate fibers, but they are formed by different weaving methods. The hydrophobic fabric EF1 and the hydrophilic fabric EF2 were cut into 1 $cm^2$ circles respectively, and the dry weights Wa of the fabrics were measured. After that, 50 µl of water was given to the hydrophobic fabric EF1 and the hydrophilic fabric EF2, and the wet weights Wb of the fabrics were measured. After that, the water absorption rate (%) could be obtained by the following (Formula 2):

Water absorption rate (%)=(Wb−Wa)/Wa×100%  (Formula 2)

Table 1 provides evaluation results for the water content of the hydrophobic fabric EF1 according to an embodiment of the present disclosure and the hydrophilic fabric EF2 according to an embodiment of the present disclosure.

TABLE 1

| Sample | Water absorption rate(%) |
|---|---|
| EF1 | −7.7% |
| EF2 | 236.8% |

From the results in Table 1, it can be seen that the water content of the hydrophilic fabric EF2 is higher than the water content of the hydrophobic fabric EF1. Polyethyleneterephthalate materials will affect the water absorption capacity according to the different weaving forms. The higher water absorption rate is designed as the inner water absorption layer, which can absorb and retain blood and biological active factors, and the lower water absorption rate is designed as the outer waterproof layer.

FIGS. 6A to 6C, 7A to 7C, and 8A to 8C illustrate the evaluation of the diffusion effect of the hydrophobic fabric EF1, the hydrophilic fabric EF2, and the control group EF3 to simulate the effect of preventing enzyme interference in the joint capsule.

Example 2

Experiments for Testing the Polyethyleneterephthalate Fiber in Penetration/Barrier to Enzyme In the test groups, the hydrophobic fabric EF1 and the hydrophilic fabric EF2 as described above were respectively placed in the connector T2. In the control group EF3, no fabric was placed in the connector T2. The connector T2 was communicated with the common tube T1R on the right and the common tube T1L on the left, respectively. The common tube T1L on the left side of the connector T2 was filled with water (for example 3.5 ml), and the common tube T1R on the right side of the connector T2 was filled with 2% (wt %) red food coloring (MW: 604.5 Da), and the diffusion of red food coloring was observed by imaging at 0 hours, 4 hours and 21 hours, respectively.

Figure 6A:
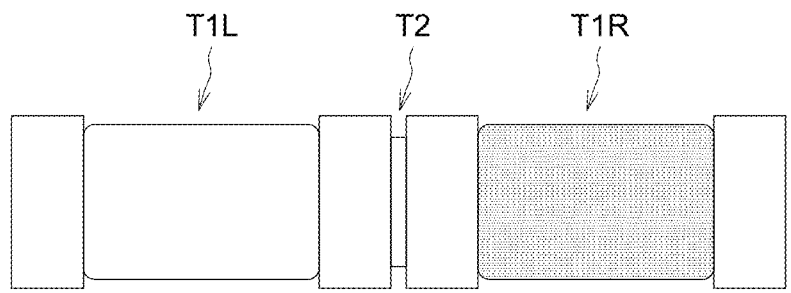
FIGS. 6A-6C, 7A-7C, and 8A-8C illustrate the evaluation of the diffusion effect of the hydrophobic fabric, the hydrophilic fabric and the control group of the present disclosure.
Figure 6B:
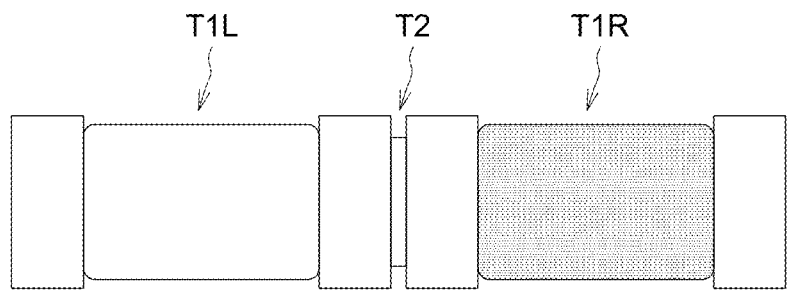
Figure 6C:
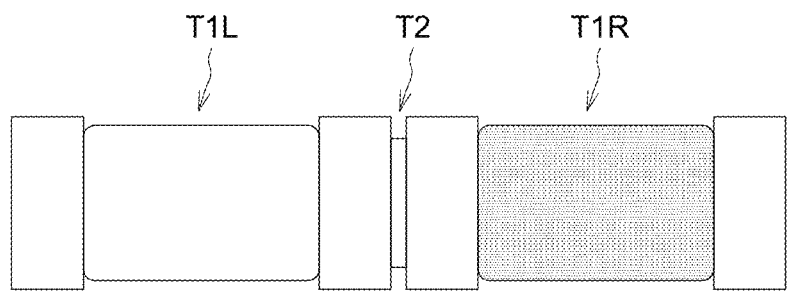
Figure 7A:
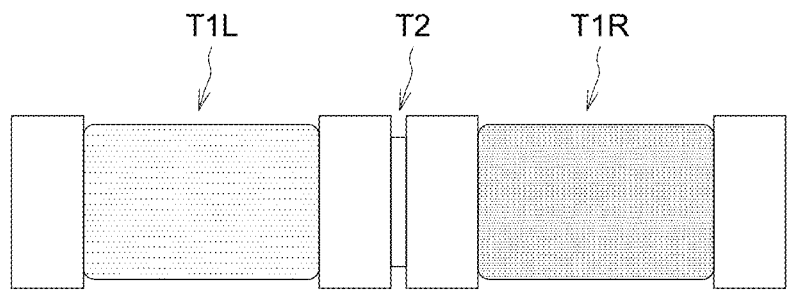
Figure 7B:
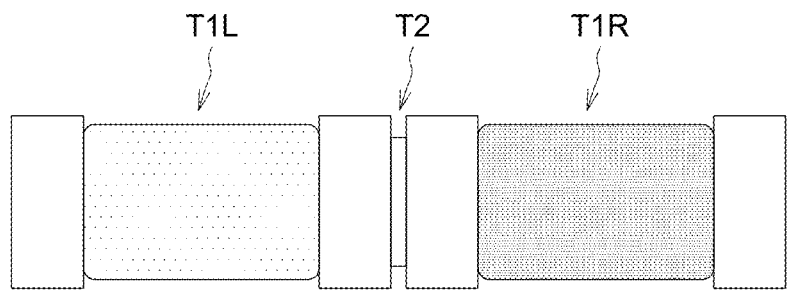
Figure 7C:
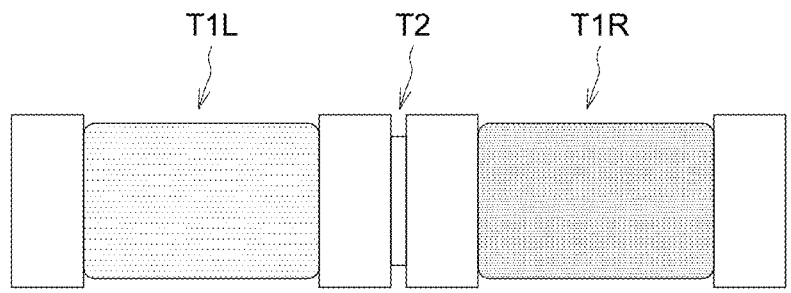
Figure 8A:
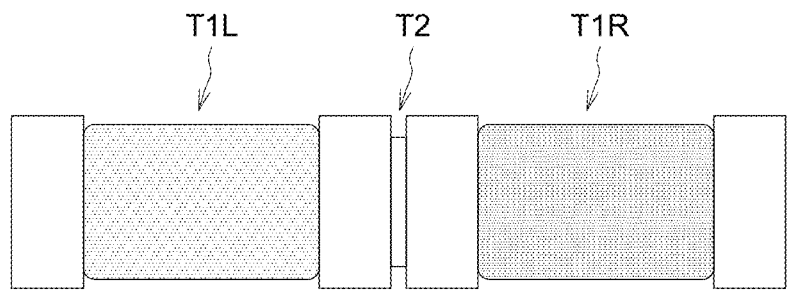
Figure 8B:
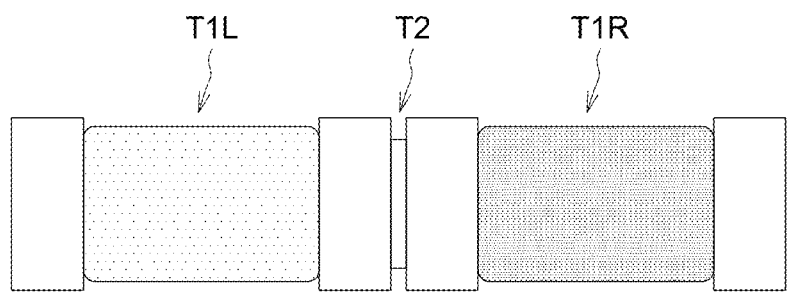
Figure 8C:
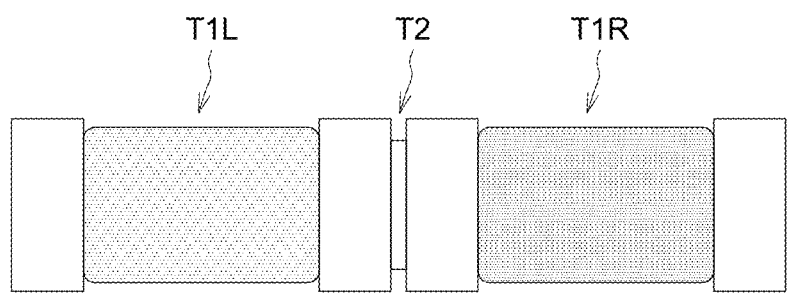

The results can be shown in the following figures. FIG. 6A shows the diffusion status of red food coloring in the hydrophilic fabric EF2 group at 0 hours; FIG. 6B shows the diffusion status of red food coloring in the hydrophobic fabric EF1 group at 0 hours; FIG. 6C shows the diffusion status of red food coloring in the control group at 0 hours. FIG. 7A shows the diffusion status of red food coloring in the hydrophilic fabric EF2 group at 4 hours; FIG. 7B shows the diffusion status of red food coloring in the hydrophobic fabric EF1 group at 4 hours; FIG. 7C shows the diffusion status of red food coloring in the control group at 4 hours. FIG. 8A shows the diffusion status of red food coloring in the hydrophilic fabric EF2 group at 21 hours; FIG. 8B shows the diffusion status of red food coloring in the hydrophobic fabric EF1 group at 21 hours; FIG. 8C shows the diffusion status of red food coloring in the control group at 21 hours.

It can be seen from the figures that the higher the density of the dots in the common tube T1L on the left, the more red food coloring diffuses from the common tube T1R on the right to the common tube T1L on the left, and the effect of blocking the red food coloring from diffusion becomes worse. Conversely, when the dot density in the common tube T1L on the left is lower, it indicates that the less red food coloring diffuses from the common tube T1R on the right to the common tube T1L on the left, and the better the effect of blocking the diffusion of the red food coloring.

It can be seen from the results that the hydrophobic fabric EF1 has a better effect on preventing the diffusion of red food coloring than the hydrophilic fabric EF2 and the control group. After 21 hours of action, the amount of the red food coloring diffused to the common tube T1L on the left in the hydrophobic fabric EF1 group is still much lower than the amount of the red food coloring diffused to the common tube T1L on the left in hydrophilic fabric EF2 group and the control group. The molecular weight of the enzyme (uPA) in the joint capsule is 31.1 kDa, which is larger than the molecular weight of the pigment. Therefore, the hydrophobic fabric EF1 according to an embodiment of the present disclosure can indeed reduce enzyme interference, improve the success rate of surgery, and assist ligament repair.

Animal Experiments

The Lanyu pigs were used as the animal model of anterior cruciate ligament injury in the present disclosure. Analgesics, antibiotics and anesthetics were administered before surgery. The operation procedure of "test group TG" is as followed. The knee joint of the Lanyu pig was cut, and looked for the anterior cruciate ligament. The anterior cruciate ligament was cut in half with the scalpel at the position about 3~5 mm away from the femoral end, to simulate a torn injury of the anterior cruciate ligament. Next, the tissue repair device 100 according to an embodiment of the present disclosure was used to cover the injured position of the anterior cruciate ligament, that is, the tissue repair device 100 was disposed between the femur (for example, the femur UB shown in FIG. 2B) and the tibia (for example, the tibia BB shown in FIG. 2B), the inner side (hydrophilic fabric fiber) of the tissue repair device 100 was attached to the meniscus, and the tissue repair device 100 was compressed and fixed to the anterior cruciate ligament by a wire (for example, the wire 130 shown in FIGS. 1A and 1B), which is similar to the state shown in FIG. 2C. After that, the whole blood (similar to the repair liquid RL shown in FIG. 2D) of the tested pig was injected into the accommodating space of the inner layer of the tissue repair device 100 and into the joint cavity, and then the various layers of tissue and skin were sutured to complete the operation. The operation procedure of the "control group CG" is similar to the operation procedure of the "test group TG", the difference is that the tissue repair device 100 was not implanted into the "control group CG" pigs. The pigs in the "control group CG" and "test group TG" were sacrificed 3 months after surgery to harvest tissue specimens for the histopathological analysis.

Histopathological Analysis

Pigs of each group were sacrificed and the anterior cruciate ligament tissues were excised for observation, photograph and recoded. The tissues were then fixed with 10% neutral formalin. Subsequently, samples of the anterior cruciate ligament tissues were processed with dehydration, transparency, paraffin wax immersion and paraffin embedding. After that, the samples of the anterior cruciate ligament tissues were cut into tissue sections of 5 μm, and stained with hematoxylin and eosin (H&E) and Masson's trichrome. Damage or repair conditions of the tissue samples in each group were finally observed with an optical microscope.

Results

Figure 9A:
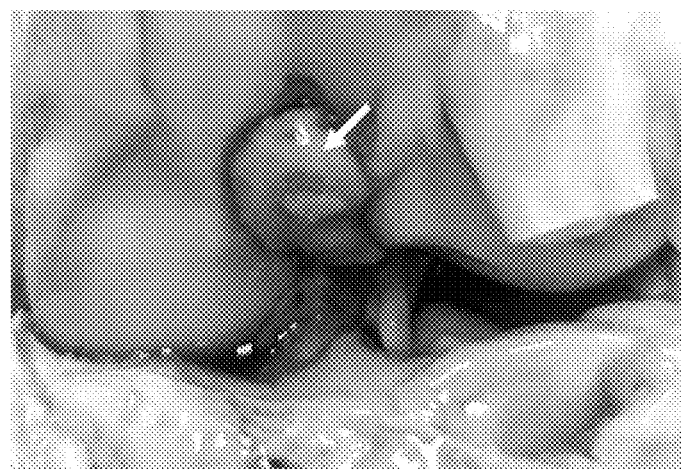
FIG. 9A shows a photograph for the appearance of the damaged cruciate ligament tissue in the "control group CG".
Figure 9B:
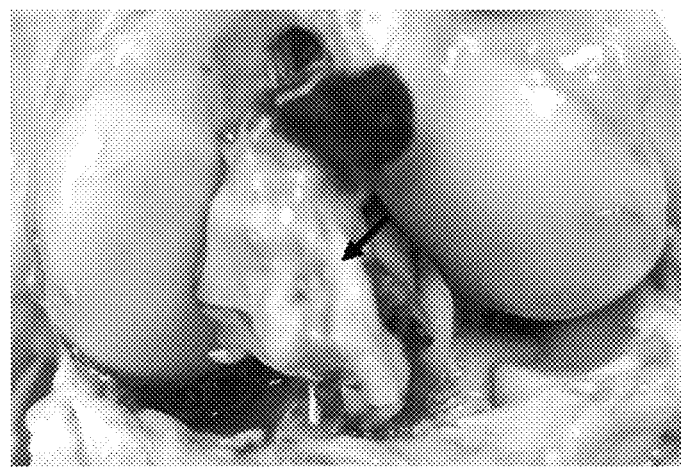
FIG. 9B shows a photograph for the appearance of the anterior cruciate ligament tissue after repair in the "test group TG".

FIG. 9A shows a photograph of the macroscopic observations of the anterior cruciate ligament tissue in the "control group CG". FIG. 9B shows the macroscopic observations of the anterior cruciate ligament tissue in the "test group TG". The arrows indicate the locations of the anterior cruciate ligament tissues.

Referring to FIG. 9A, the anterior cruciate ligament tissue in the "control group CG" has been complete tear. In contrast, referring to FIG. 9B, the anterior cruciate ligament tissue in the "test group TG" is visibly regenerated, indicating that the injury of the anterior cruciate ligament tissue has been repaired.

Figure 10A:
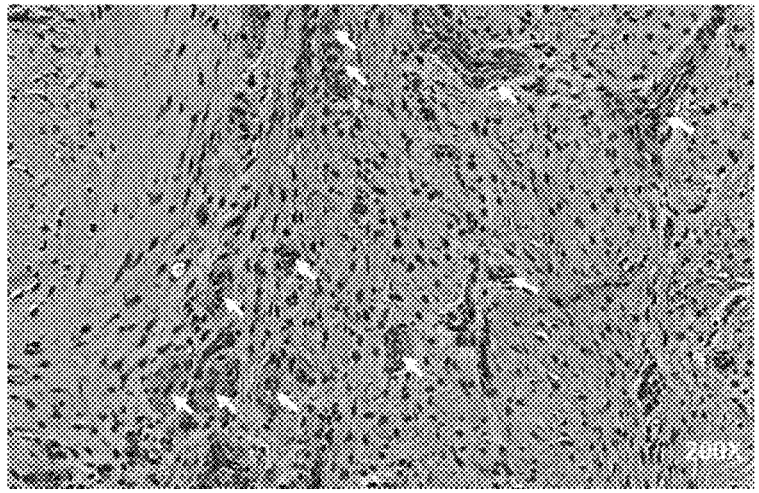
FIG. 10A shows the results of hematoxylin and eosin (H&E) stain of the anterior cruciate ligament tissue section in the "control group CG".
Figure 10B:
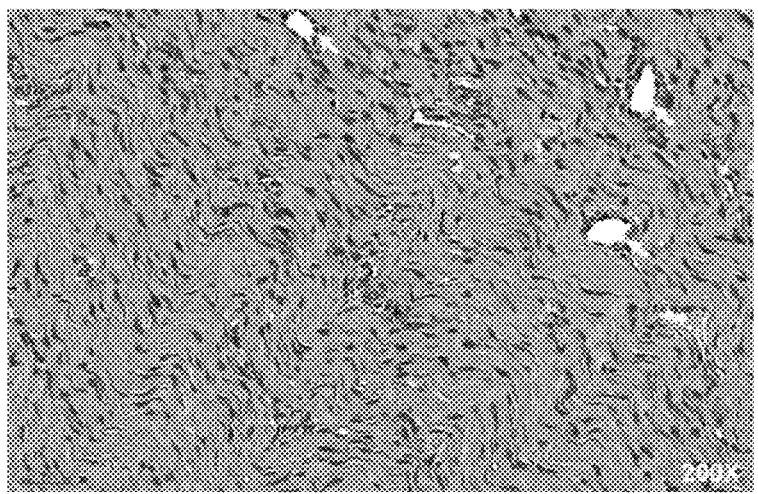
FIG. 10B shows the results of hematoxylin and eosin (H&E) stain of the anterior cruciate ligament tissue section in the "test group TG".
Figure 11A:
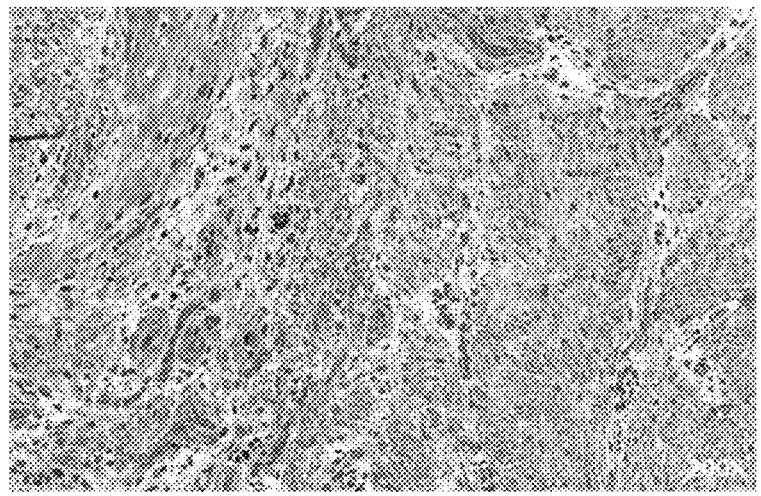
FIG. 11A shows the results of Masson's trichrome stain of the anterior cruciate ligament tissue section in the "control group CG".
Figure 11B:
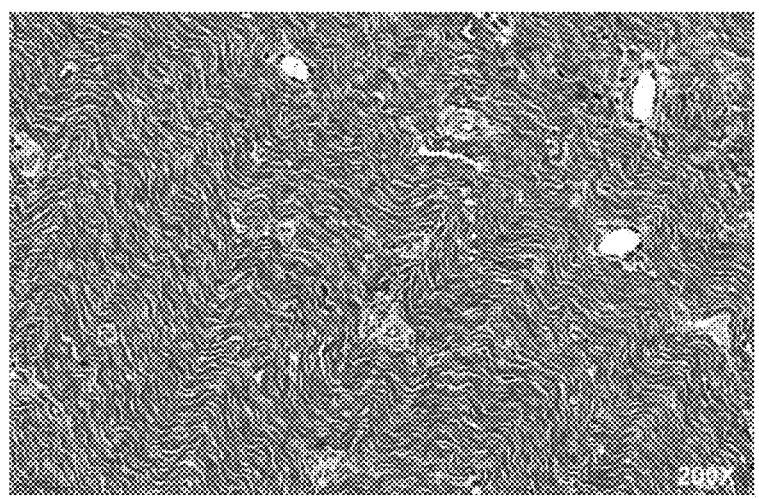
FIG. 11B shows the results of Masson's trichrome stain of the anterior cruciate ligament tissue section in the "test group TG".

FIG. 10A shows the results of hematoxylin and eosin stain of the anterior cruciate ligament tissue section in the "control group CG". FIG. 10B shows the results of hematoxylin and eosin stain of the anterior cruciate ligament tissue section in the "test group TG". FIG. 11A shows the results of Masson's trichrome stain of the anterior cruciate ligament tissue section in the "control CG". FIG. 11B shows the results of Masson's trichrome stain of the anterior cruciate ligament tissue section in the "test group TG". The arrows indicate the positions of the blood vessels.

Refer to FIGS. 10A-11B simultaneously, compared to the anterior cruciate ligament tissue in the "control group CG", the diameter of collagen fibers is larger with more directionality and density in the "test group TG". In addition, the ratio of matrix is higher with lesser the angiogenesis which indicated that the injury of the anterior cruciate ligament tissue has been well repaired. Conversely, in the anterior cruciate ligament tissue of the "control group CG", the diameter of collagen fibers is smaller, the arrangement of collagen fibers is disorganized and loose, the ratio of matrix is lower, and the angiogenesis is increased, indicating that the injury of the anterior cruciate ligament tissue has not been repaired.

From the above results, the tissue repair device 100 in the test group TG effectively repaired the injured anterior cruciate ligament at the injured position of the anterior cruciate ligament tissue. If there were no treatment for the injured anterior cruciate ligament, the injured anterior cruciate ligament would be difficult to repair. After 3 months, the injured anterior cruciate ligament would still be in a damaged state, or worse, lead to the rupture of the ligament, as shown in the anterior cruciate ligament in the control group CG.

According to an embodiment of the present disclosure, a tissue repair device is provided. The tissue repair device includes a body portion and at least one wire. The body portion includes an inner layer and an outer layer. The inner layer is closer to a tissue than the outer layer, wherein the inner layer includes a hydrophilic structure, and the outer layer includes a hydrophobic structure. The wire is connected to the body portion to fix the body portion on the tissue.

Since the tissue repair device of an embodiment of the present disclosure includes an inner layer and an outer layer, the inner layer includes a hydrophilic structure, which can retain the content of blood or other biologically functional substances; the outer layer includes a hydrophobic structure, which can prevent enzymes from interfering with the tissue repair. Therefore, the tissue repair device of one embodiment of the present disclosure can improve the repair condition of the tissue. Furthermore, the tissue repair device disclosed in the present disclosure is easy to operate and can be easily fixed to the injured position of the tissue. It is suitable for minimally invasive surgery, arthroscopic operation or other surgical operations, which can save the time spent on the operation and greatly increase the success rate of the operation.

In summary, although the present disclosure has been disclosed in the above embodiments, it is not intended to limit the present disclosure. Those ordinary skilled in the technical field can make various changes and modifications without departing from the spirit and scope of the present disclosure. Therefore, the protection scope of the present disclosure shall be subject to those defined by the following claims.

What is claimed is:

1. A tissue-repair device for repairing a tissue, the tissue-repair device comprising:
    a body portion comprising an inner layer and an outer layer, the inner layer being configured to be close to the tissue, wherein the inner layer comprises a hydrophilic structure, and the outer layer comprises a hydrophobic structure,
    the body portion comprising an upper opening and a lower opening communicating with each other, and the body portion surrounding an injured position of the tissue;
    the body portion comprising:
    a middle portion;
    an edge portion connected to the middle portion, and the edge portion comprising a first edge portion and a second edge portion,
    wherein the middle portion is disposed between the first edge portion and the second edge portion, the first edge portion corresponds to the upper opening, and the second edge portion corresponds to the lower opening; and
    a plurality of holes disposed on the first edge portion and the second edge portion; and
    at least one wire comprising a first wire and a second wire, wherein the first wire passes through the holes disposed in the first edge portion, the second wire passes through the holes disposed in the second edge portion, when the body portion surrounds the injured position, the first edge portion and the second edge portion approach toward the tissue by tightening the first wire and the second wire, in order to fix the body portion to the tissue.

2. The tissue-repair device according to claim 1, wherein the outer layer is a hollow cylindrical structure, the inner layer is a spiral structure, and the inner layer extends from the upper opening to the lower opening in the middle portion.

3. The tissue-repair device according to claim 1, wherein the outer layer is a hollow cylindrical structure, the inner layer comprises a plurality of ring structures, and the ring structures are separated from each other and are disposed along a direction extending from the upper opening to the lower opening in the middle portion.

4. The tissue-repair device according to claim 1, wherein a height of the body portion is adjustable in a first direction and the first direction is parallel to a direction extending from the upper opening to the lower opening.

5. The tissue-repair device according to claim 4, wherein, before the body portion surrounds the injured position, the body portion has a first height in the first direction; after the body portion is fixed to the tissue, the body portion has a second height in the first direction, and the second height is greater than the first height.

6. The tissue-repair device according to claim 1, wherein the hydrophobic structure comprises a hydrophobic fabric, and the hydrophobic fabric comprises polyethylene terephthalate fiber.

7. The tissue-repair device according to claim 6, wherein the hydrophobic fabric has a fiber fineness of 0.00002 dtex to 0.022 dtex.

8. The tissue-repair device according to claim 6, wherein the hydrophobic fabric has a thickness of 0.05 mm to 0.25 mm.

9. The tissue-repair device according to claim 1, wherein the hydrophilic structure comprises a hydrophilic fabric, and the hydrophilic fabric comprises polylactic acid fiber.

10. The tissue-repair device according to claim 9, wherein the hydrophilic fabric is non-cylindrical.

11. A method for using a tissue-repair device, comprising:
providing the tissue-repair device according to claim 1;
fixing the body portion on the tissue by the first wire and the second wire, so that the inner layer surrounds the injured position to form an accommodating space; and
injecting a repair liquid into the accommodating space of the inner layer to assist in repairing the tissue.

\* \* \* \* \*